(12) United States Patent
Hillmer

(10) Patent No.: US 8,120,775 B2
(45) Date of Patent: Feb. 21, 2012

(54) SENSOR DEVICE AND FOR DETERMINING A PHYSICAL VALUE

(76) Inventor: Hartmut Hillmer, Kassel (DE)

( * ) Notice: Subject to any disclaimer, the term of this patent is extended or adjusted under 35 U.S.C. 154(b) by 464 days.

(21) Appl. No.: 11/572,722

(22) PCT Filed: Jul. 6, 2005

(86) PCT No.: PCT/DE2005/001179
§ 371 (c)(1),
(2), (4) Date: Sep. 10, 2008

(87) PCT Pub. No.: WO2006/012825
PCT Pub. Date: Feb. 9, 2006

(65) Prior Publication Data
US 2009/0141279 A1 Jun. 4, 2009

(30) Foreign Application Priority Data
Jul. 30, 2004 (DE) .......................... 10 2004 037 519

(51) Int. Cl.
*G01N 21/00* (2006.01)
*H01S 3/30* (2006.01)
(52) U.S. Cl. ............... 356/436; 356/437; 372/6; 372/22
(58) Field of Classification Search .......... 356/432–437; 372/23, 37–38, 105, 22, 28, 92, 98, 102; 250/559.4, 339.13, 343, 214 LS
See application file for complete search history.

(56) References Cited

U.S. PATENT DOCUMENTS

| | | | | | |
|---|---|---|---|---|---|
| 3,723,903 | A | * | 3/1973 | Paoli et al. ....................... | 372/28 |
| 4,423,511 | A | * | 12/1983 | Morton ........................... | 372/95 |
| 4,822,169 | A | * | 4/1989 | Distl et al. ..................... | 356/364 |
| 5,263,038 | A | * | 11/1993 | Lukas et al. .................... | 372/22 |
| 5,351,253 | A | * | 9/1994 | Wong .......................... | 372/29.02 |
| 5,377,212 | A | * | 12/1994 | Tatsuno et al. ................. | 372/22 |
| 5,448,657 | A | | 9/1995 | Kim et al. | |
| 5,841,797 | A | * | 11/1998 | Ventrudo et al. .................. | 372/6 |
| 5,940,419 | A | * | 8/1999 | Xie ................................ | 372/22 |
| 6,041,072 | A | * | 3/2000 | Ventrudo et al. ............... | 372/102 |
| 6,075,252 | A | * | 6/2000 | Atkinson et al. ........... | 250/559.4 |
| 6,353,225 | B1 | * | 3/2002 | Strzoda et al. ........... | 250/339.13 |
| 6,442,187 | B1 | * | 8/2002 | Dutov et al. .................. | 372/101 |
| 6,597,017 | B1 | * | 7/2003 | Seko et al. ....................... | 257/79 |

(Continued)

FOREIGN PATENT DOCUMENTS

DE  38 36 116  4/1990

(Continued)

OTHER PUBLICATIONS

Lacot E,. et al: "Spectrotemporal Dynamics of a Two-Coupled Mode Laser" Physical Review A, vol. 57, No. 5, May 1998, pp. 4019-4025, XP002350006.

Baev V M and Toschek P E: "Sensitivity Limits of Laser Intracavity Spectroscopy" Proc. SPIE, vol. 1715, 1992, pp. 381-392, XP002350007.

(Continued)

*Primary Examiner* — Sang Nguyen
(74) *Attorney, Agent, or Firm* — Michael J. Striker

(57) ABSTRACT

A sensor device for determining a physical value using a laser, whose emission behavior can be affected by the physical value is described. The laser is arranged to emit at least two concurrent modes lying above a laser threshold and the physical value is determined using a comparison of changes of the at least two modes occurring under the influence of the physical value.

28 Claims, 15 Drawing Sheets

U.S. PATENT DOCUMENTS

| | | | |
|---|---|---|---|
| 6,757,245 B1 * | 6/2004 | Kuusinen et al. | 370/230 |
| 7,012,944 B2 * | 3/2006 | Lee et al. | 372/50.1 |
| 7,027,467 B2 * | 4/2006 | Baev et al. | 372/6 |
| 7,251,023 B2 * | 7/2007 | Bohnert et al. | 356/73.1 |
| 7,313,424 B2 * | 12/2007 | Mayevsky et al. | 600/310 |
| 7,376,164 B2 * | 5/2008 | Takahashi | 372/50.1 |
| 2004/0069948 A1 | 4/2004 | Feisst et al. | |
| 2005/0110992 A1 | 5/2005 | Scherer et al. | |

FOREIGN PATENT DOCUMENTS

| | | |
|---|---|---|
| DE | 197 17 145 | 10/1998 |
| DE | 100 63 151 | 6/2002 |
| DE | 100 63 678 | 7/2002 |
| DE | 101 19 618 | 10/2002 |

OTHER PUBLICATIONS

Meissner K E et al: "Surfaceemitting Semiconductor Laser for Intracavity Spectroscopy and Microscopy" Proc. SPIE, vol. 2399, 1995, pp. 561-570, XP002350008.

Weng W W et al: Design, Fabrication, and Performance of Infrared and Visible Vertical-Cavity Surface-Emitting Lasers IEEE Journal of Quantum Electronics, vol. 33, No. 10, Oct. 10, 1997, pp. 1810-1824, XP002350009.

Loncar M et al: "Low-Threshold Photonic Crystal Laser" Applied Physics Letters, AIP, American Institute of Physics, Melville, NY, US, vol. 81, No. 15, Oct. 7, 2002, pp. 2680-2682, XP001142137, ISSN: 0003-6951.

\* cited by examiner

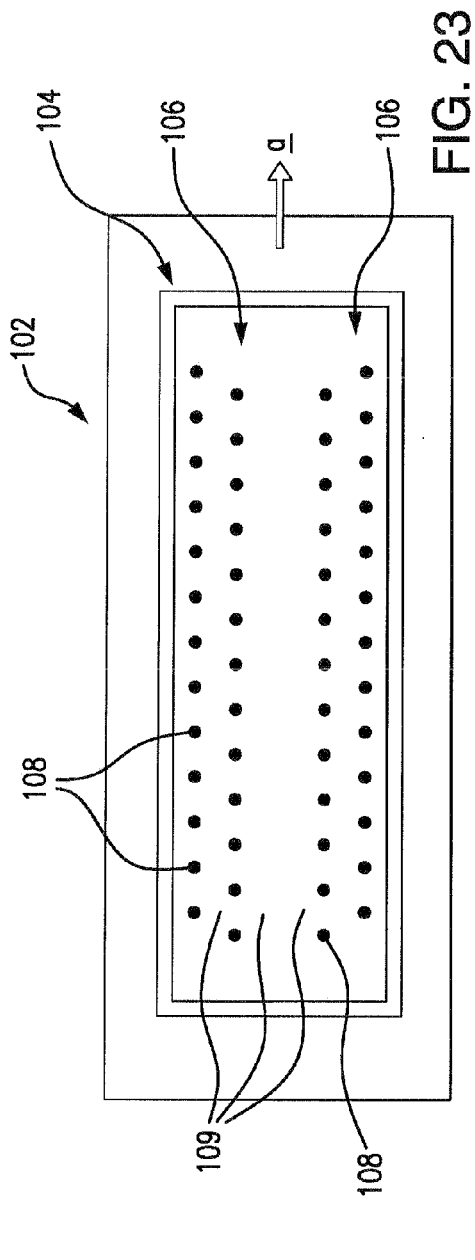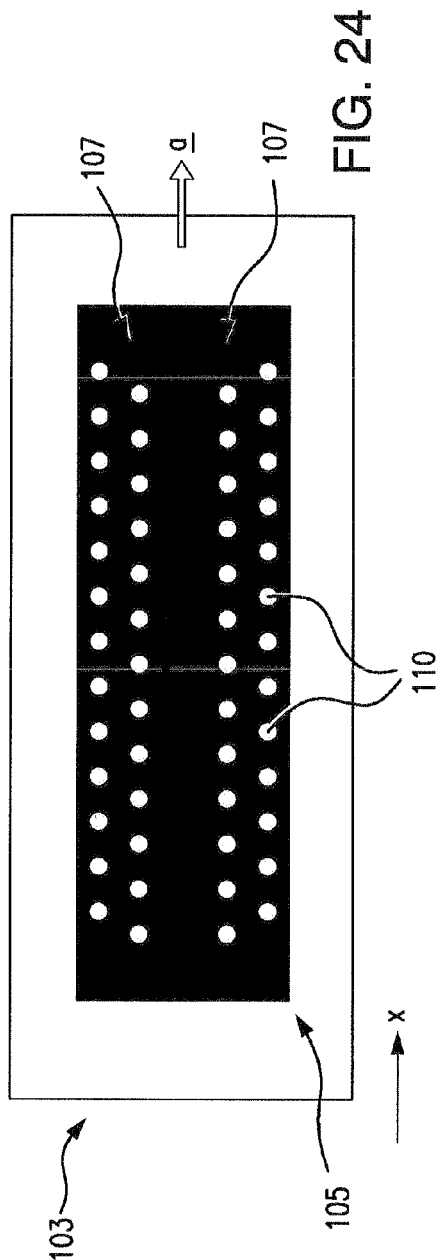

SENSOR DEVICE AND FOR DETERMINING A PHYSICAL VALUE

CROSS-REFERENCE TO RELATED APPLICATION

The invention described and claimed hereinbelow is also described in German Patent Application DE 10 2004 037 519.4, filed on Jul. 30, 2004. The German Patent Application, whose subject matter is incorporated herein by reference, provides the basis for a claim of priority of invention under 35 U.S.C. 119(a)-(d).

BACKGROUND OF THE INVENTION

This invention relates to a sensor device of the kind specified in the pre-characterizing part of claim 1 and a method according to the pre-characterizing part of claim 19.

In known devices and methods, e.g. the optical absorption or the absorption power of a chemical substance, especially a fluid, (e.g. DE 197 17 145 C2, DE 100 63 678 A1) is determined as a physical value. A laser diode emitting a single mode is tuned through a predetermined wavelength range, in order to sweep through at least one characteristic absorption line in the spectrum of a fluid to be detected. The tuning of the laser diodes is effected by variation of its working temperature for example.

A problem with such sensor devices is represented by the small interaction length of the light with the fluid molecules to be detected. It is therefore already known also the increase the effective length of interaction of the sensor device by using a micro-resonator in the form of a photonic crystal, which simultaneously conflicts with the desire for miniaturisation. Either light emitted by an external light source, e.g. a laser, is passed through the photonic crystal through which the fluid flows (e.g. DE 100 63 151 A1) or the photonic crystal together with a laser active material are so combined in a laser that the gas flowing through the resonator directly affects the laser characteristics or the emission behaviour of the laser (e.g. DE 101 19 618 A1). The nature or the concentration of the fluid can be inferred from the change in the emission characteristic.

The detection sensitivity of such fluid sensors has however not been found sufficient for practical applications, especially when it is to be used for qualitative or quantitative detection of toxic fluids in particular, or fluids which are especially dangerous for other reasons.

In the case of a fluid sensor, the optical absorption as physical value effects attenuation of the intensity of the radiated light and thus an alteration of the emission behaviour of the laser.

SUMMARY OF THE INVENTION

The technical problem of the present invention therefore lies in so designing the sensor device and the method of the kinds initially specified that numerous different physical values and especially their changes can be determined with high sensitivity and accuracy, in spite of a miniaturised construction.

The characterizing feature of claims 1 and 19 serve to solve this problem.

While attempts have constantly been made previously to operate a laser diode in a single mode and suppress subsidiary modes, apart from in direct applications (e.g. welding, soldering or boring) the purpose of the present invention is make use of a laser with more than one mode occurring in operation in mode competition. Use is made of the fact that the comparatively unstable mode equilibrium of a laser operated with multiple modes is markedly distorted even by small changes or numerous influencing values, such as temperature, injection current or geometric resonator properties for example. These influencing values are used in accordance with the invention either directly as the physical values to be determined or indirectly for measuring dependent values, such as lengths, volumes, refractive index, electrical field, magnetic field, pressure, optical absorption or the like for example. In principle the sensor device according to the invention is suitable for determining all physical values which directly or indirectly affect the emission behaviour of a laser as such or can be derived from such values affecting the emission behaviour.

The invention further concerns the concept that even an extremely small effect on the laser emission caused by a physical value leads to a substantially more marked change in the modes in multi-mode laser operation than can be observed in single mode operation. This can involve changes in the amplitudes, intensities or spectral positions or distributions of the modes for example, especially if a laser is operated with more than two modes. In addition there is the advantage that the same measured signal, e.g. the intensity or the change in intensity or an electrical characteristic value can be used each time to determine a plurality of physical values.

Further advantageous features of the invention appear from the dependent claims.

BRIEF DESCRIPTION OF THE DRAWINGS

The invention will now be explained in more detail in conjunction with the accompanying drawings of embodiments, wherein:

FIGS. 12 to 24 show further embodiments of the sensor device according to the invention for detecting and concentration measurement of a chemical substance.

DESCRIPTION OF THE PREFERRED EMBODIMENTS

Figure 1:
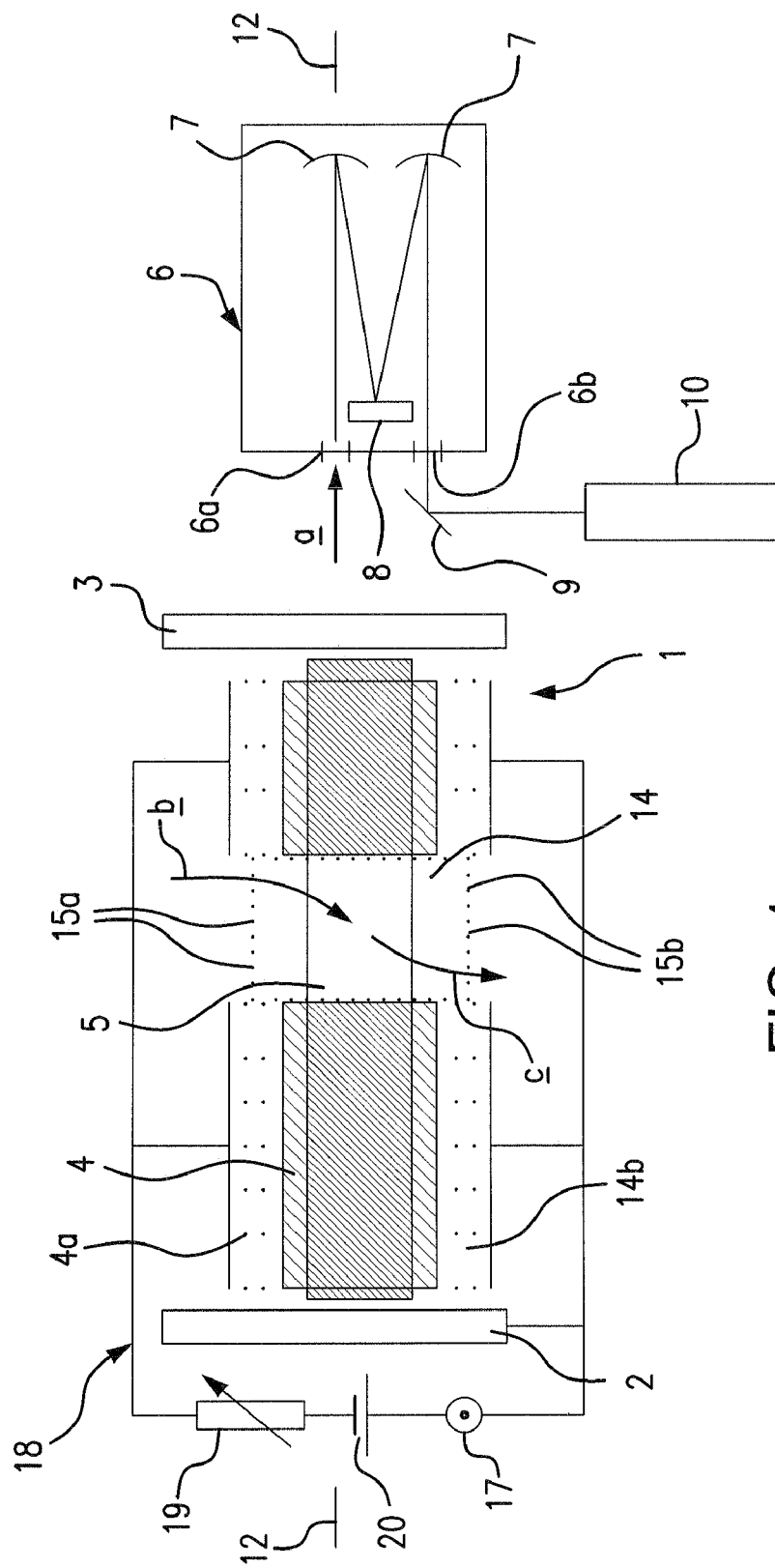
FIG. 1 is a schematic representation of a first embodiment of the sensor device according to the invention adapted for detecting and for concentration measurement of a chemical substance.

FIG. 1 shows a sensor device according to the invention for detecting a chemical substance in the form of a fluid by detecting the absorption of laser light. Use is made of the fact that the fluid can identified and quantitatively detected on the basis of its characteristic absorption bands or lines.

The sensor device includes a laser 1 schematically shown in FIG. 1 and preferably implemented as a solid body laser 1, with a horizontal resonator bounded by two resonator mirrors 2 and 3. In between the resonator mirrors 2, 3 is disposed an active laser medium 4 of the laser 1, with a semiconductor layer 4a, 4b on each of its broad sides. The reflectivity of the resonator mirror 3 is smaller than 100%, so that part of the light 5 optically amplified in the active medium 4 and reflected between the mirrors 2 and 3 emerges from the resonator mirror 3. The light 5 emerging from the resonator mirror 3 and indicated by an arrow a is passed into the entrance slit 6a of a monochromatic filter 6 for example. Within the monochromatic filter 6 the light is so reflected at deflecting mirrors 7 and an optical grating 8 that is emerges from an outlet slit 6b of the monochromatic filter 6. The light emerging from the monochromatic filter 6 is passed through a deflecting element 9 to a photodetector 10.

The active laser medium 4 is interrupted or traversed by a receiving space 14 for a fluid, like a hollow body perpendicular to a horizontal axis 12 of the laser 1, which fluid can be for example a gas, a liquid, an air-fluid mixture or mixture of a carrier gas and a fluid to be identified and possible detrimental to health. The receiving space 14 has inlet and outlet openings 15a, 15b for the fluid at its sides respectively parallel to the axis 12, while the passage of the laser light 5 takes place at its end sides disposed perpendicular to the axis 12. In order to identify the fluid this is, as shown simplified by the arrows b and c, passed by means of the openings 15a, b through the receiving space 14. The fluid interacts in the receiving space 14 with the light 5 reflected to and fro in the laser 1.

Figure 2A:
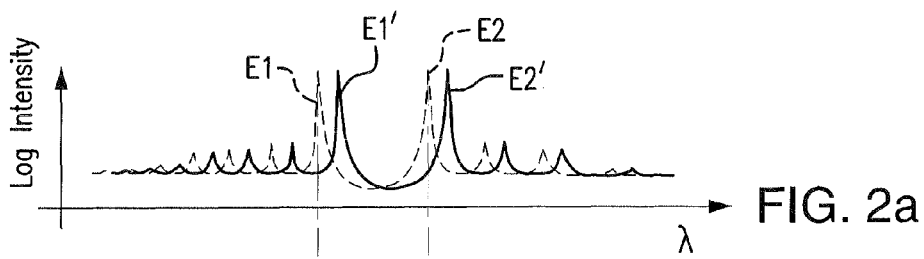
FIG. 2 is a schematic representation of the spectral dependence of the operating or measuring values of the sensor device according to FIG. 1.
Figure 2B:
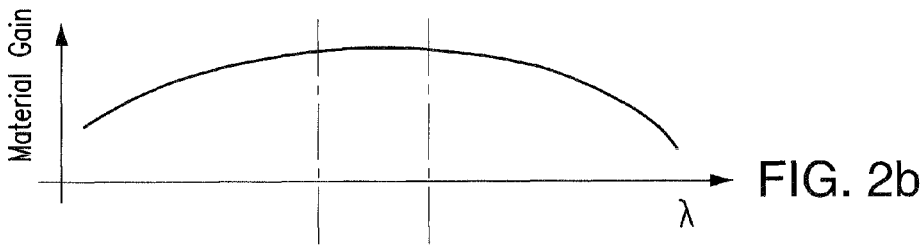
Figure 2C:
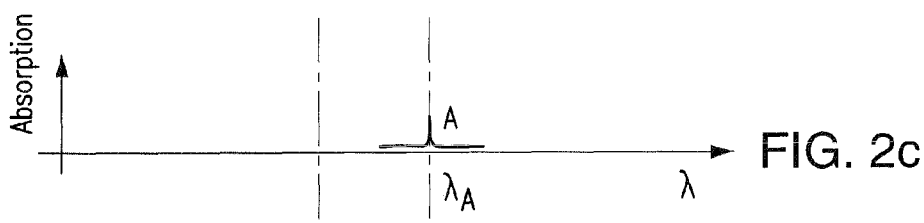
Figure 2D:
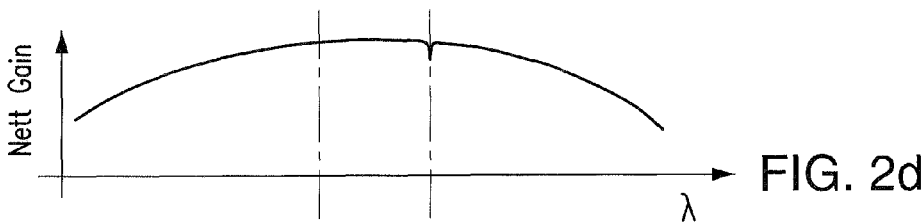

As is shown schematically in FIG. 2, a laser or a laser design is so selected in the embodiment that the light emission takes place in two modes and the laser 1 radiates in two modes E1' and E2' according to FIG. 2(a). One mode is so selected that it lies spectrally in the region of a known absorption line characteristic of the fluid to be identified or a corresponding adsorption band A at a wavelength $\lambda_A$ according to FIG. 2(c). The operating parameters are preferably so adjusted that the mode spectrum shown in FIG. 2(a) emits two dominant modes E1', E2' lying above the laser threshold and otherwise markedly weaker subsidiary modes, wherein the modes E1', E2' are moreover on conflict in relation to the optical amplification, i.e. are in competition. Such a mode of operation is, as mentioned initially, undesirable as a rule, since the laser 1 does not run stably enough and the intensity of even the strongest modes E1', E2' according to FIG. 2(a) mostly lie markedly below the intensity attainable in a single mode emission mode.

Since the spectral location of a laser more in multi-mode operation depends very sensitively on the current operating parameters, the absolute mode wavelength can be predetermined only with difficulty. In the normal case therefore, none of the modes E1', E2' of the laser shown in FIG. 2 can be matched spectrally exactly with the characteristic absorption line A of the fluid. However, as a rule at least one of the modes can be so tuned that it lies spectrally close enough to the absorption line A. The laser 1 can then be tuned, for example by altering an electrical injection current which serves to create a population inversion in the semiconductor laser structure, by altering the working temperature by means of a heat sink (e.g. heating element of Peltier element), or otherwise, so that one of the two modes E1' and E2', preferably essentially of like strength, whose intensity difference preferably amounts to only a few dB matches spectrally the absorption band A of the fluid. This is indicated in FIG. 2(a) for the mode E2' displaced to E2, while the mode E1' has been shifted to E1'. The emission spectrum thus obtained with the main modes E1, E2 and the wavelengths $\lambda_1$ and $\lambda_2$ is indicated in FIG. 2(a) by a broken line. The tuning ability of the laser 1, for example concurrently with the aid of the injection current and the temperature, has the advantage that the intensities of the modes E1, E2 obtained after the tuning can be adjusted to values of approximately equal magnitude, i.e. the dual mode condition is not affected simply by the tuning of the laser 1.

The manner of operation of the described sensor device is essentially as follows:

Through the optical excitation of the absorption of the fluid underlying the absorption band A through laser light of the wavelength $\lambda_2 = \lambda_A$, the light of the wavelength $\lambda_2 = \lambda_A$, is attenuated in each passage through the fluid. Accordingly the light amplification required the laser process through stimulated emission is reduced for the mode E2 [FIG. 2(d)], which means is selectively reduced at the wavelength $\lambda_2 = \lambda_A$. At the wavelength $\lambda_2 = \lambda_A$, a dip results in the amplification characteristic. The setting of the population inversion in the active laser medium 4 is not affected substantially by this. The electrons used to create a population inversion into an energetically higher state are available as before for a transition into an energetic ground f state with emission of a photon available. Since the stimulated emission outweighs the spontaneous emission, the electrons in the higher energy state cannot be excited by a stimulation of the mode E1 not affected by absorption processes or the like substantially more efficiently than a transition into the ground state by emission of a photon of the wavelength $\lambda_1$. Thus an enhancement of the intensity of the mode E1 and a reduction in the intensity of the mode E2 are observed [FIG. 2(e)]. In other words, the extremely small reduction of the effective gain [FIG. 2(d)] precisely at the absorption line A (spectral hole burning) effects a dramatic corresponding intensity difference between the two modes.

The emission spectrum of the laser 1 is recorded with the aid of the monochromatic filter 6 (FIG. 1) and the photodetector 10. Then for example the difference $\Delta I$ of the spectroscopically determined intensity maxima of the two modes E1 and E2 is determined by a comparator 11. That is, comparator 11 compares, and determines the difference $\Delta I$ between the intensity maxima of mode E1 and intensity maxima of mode E2. The fluid concentration can also be determined from this difference $\Delta I$ with the aid of a calibration carried out previously for the fluid. Such a calibration can be effected for example in that known fluid concentrations are created in the receiving space 14 and the corresponding differences $\Delta I$ of the intensity maxima of the two modes E1 and E2 are determined. To this end, it can be advantageous to close the inlet and outlet openings 15a, 15b by covers, in order to enclose precisely determined amounts of fluid in the receiving space 14 each time during the calibration.

Figure 2E:
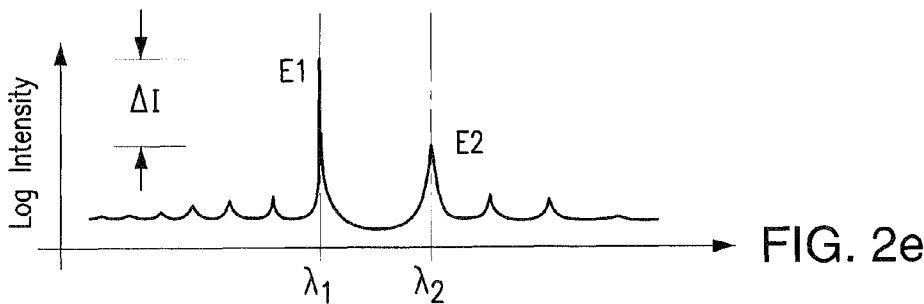

As is apparent from FIG. 2(e), not only is the intensity of the emission mode E2 reduced compared with its intensity in the absence of the fluid, but at the same time the intensity of the mode E1 relative to its intensity in the absence of the fluid is amplified. The resulting relative intensity changes $\Delta I$ of the two modes E1 and E2 lead to a strong measuring signal. Since the two modes E1 and E2 are in competition with one another, the intensity change of the mode E1 which is not directly affect can in particular be very much greater that the intensity of the mode E2 affected by absorption. It can be seen from the logarithmic representation of FIG. 2(e) that intensity changes of up to orders of magnitude can be observed. Accordingly a high sensitivity and accuracy are achieved both in qualitative and quantitative respects.

So long as the amount of the fluid passed through the laser resonator is sufficient to alter the refractive index in the resonator and thus its optical length, an unequal spectral shift of the two modes E1 and E2 is obtained, as well as the change of the relative intensities of the two modes E1, E2, which by analogy with FIG. 2(a) can lead to alteration of their original spectral spacing Δλ.

The invention thus relies on a laser whose mode competition is affected very sensitively by the physical value to be detected (absorption of the fluid). The sensor signal can also be determined from electronic parameters.

Since the dynamics of the charge carrier density (electronic) in the active zone of the laser and the photon density (photonic) in the individual modes are closely correlated in the resonator through the laser rate equations, all elements observable in the spectrum can also be found in electrical values. This makes it possible to replace the relatively expensive optical measurement explained with reference to FIG. 1 by the measurement of an electronic value, for example the noise (for example the relative intensity noise). Through the correlation of the charge carrier and photon densities, the same information can be extracted from the noise, likewise after prior calibration, i.e. a corresponding molecular concentration can be "measured" here also, which implements a very cost effective measuring possibility.

The changes of the two modes arising from the fluid are determined for example by measuring the relative intensity noise (RIN). The relative intensity noise describes the amplitude fluctuations of an optical field and is given by the quotient of the mean quadratic intensity fluctuation of the spectral density and the mean optical power. In accordance with the invention the physical value to be measured effects a change of the at least two modes in the spectrum. An alteration of the RIN signal is involved with such a change. The stronger the optical signals of the two modes deviate from one another the smaller is the RIN signal of the laser. It is known that the relative intensity noise reduces on a transition from multi-mode operation of a semiconductor laser to single mode operation (e.g. DE 38 36 16 A1). Insofar the effect of the physical value leads to the signal of one of the two modes corresponding approximately to the background signal, i.e. a transition into a quasi single mode laser operation has taken place, the reduction of the RIN signal is especially marked and the measurement particularly simple. The RIN signal is obtained by using a photodetector and an electrical bandpass filter, e.g. as a voltage signal.

The injection current in a tailor-made laser structure can moreover be so selected that one mode of a laser in competition between two polarisations (e.g. between TE and TM). In this case the components in TE and TM polarisation are of nearly equal magnitude. In many lasers these two components also differ spectrally. This is another example of competition between two spectral components, which are called modes throughout in the context of the present invention for the sake of simplicity. Following mode combinations, given only by way of example, are conceivable: two longitudinal TE modes, two transverse TE modes, two TM modes, two transverse or longitudinal TM modes or one longitudinal TE mode and one longitudinal TM mode.

In a particularly cost effective embodiment of the sensor device according to the invention, the bistable behaviour of the two modes is used to detect a threshold value (corresponding to mode degeneration for example) or a so-called concentration threshold (e.g. toxicity limit of a poisonous molecule). The following two cases would be conceivable: (a) the fluid contains the poisonous molecule in very small concentration below the toxicity threshold value and an alarm device connected to the sensor device does not issue an alarm signal; (b) the fluid contains the poisonous molecule in higher concentration above the toxicity limit value and the alarm device issues an alarm signal. The limit value can be adjusted very precisely.

In a development of the sensor device described with reference to FIG. 1, a plurality of fluids together can be detected in parallel according to the invention through determination of the physical value "optical absorption". The laser 1 is so operated for this that it emits more than two modes, i.e. an integral number "k" of modes. A laser mode can be tuned to a characteristic absorption line of one of the plurality "k" of fluids in each of "k" different measurements. A fluid is then detected in each case by the increase in the intensity of the spectral modes not matching the absorption band of the fluid. Alternatively, apart from a reference mode, it is possible so to tune through all further k−1 modes of the k-mode laser at the same time that they matches spectrally "k−1" different absorption bands of up to "k−1" different fluids. The detection of the present fluids is then qualitatively possible through a reduction in the intensities of the "k−1" modes or extinction of the "k−1" modes and simultaneous enhancement of the intensity of the reference mode. A quantitative determination of the fluids can be made from the intensity changes by comparison with comparison measurements carried out in the same manner with known fluid amounts. A plurality of fluids can thus be detected with one sensor device. The advantage lies here in the great selectivity.

The sensor device according to the invention shown in FIG. 1 can alternatively be used also as a current sensor, as is indicated very schematically in FIG. 1. A current to be measured is for example is fed for this to a measuring terminal 17 of an injection current circuit 18 shown very much simplified and comprising the electrical supply and control elements 19, 20 for the laser 1. The current provided at the measuring terminal 17 or the change of the current flowing in the circuit 18 can be determined on the basis of a prior calibration of the mode spectrum of the laser 1 operated in two modes. This current measurement can naturally be effected only in a strong current region in which the injection current required for the operation of the semiconductor laser also when conversion of the measuring signal is omitted. However an advantage lies in that the current can be measured with great accuracy of up to tenths of a nano-ampere.

The current measurement is based in accordance with the invention on the fact that a change in the injection current for the laser 1 also causes a change of the material gain of the laser medium 4 through a change of the charge carrier distribution. The change in the material gain, especially a spectral change of the material gain, results in a directed change of the two modes. The current strength can also be determined quantitatively through a comparison of the signal strengths of the two modes with the assistance of a calibration curve. In contrast to the detection of a fluid the measured current is here the physical value, which affects the emission behaviour of the laser 1 and is thus measurable.

Figure 3:
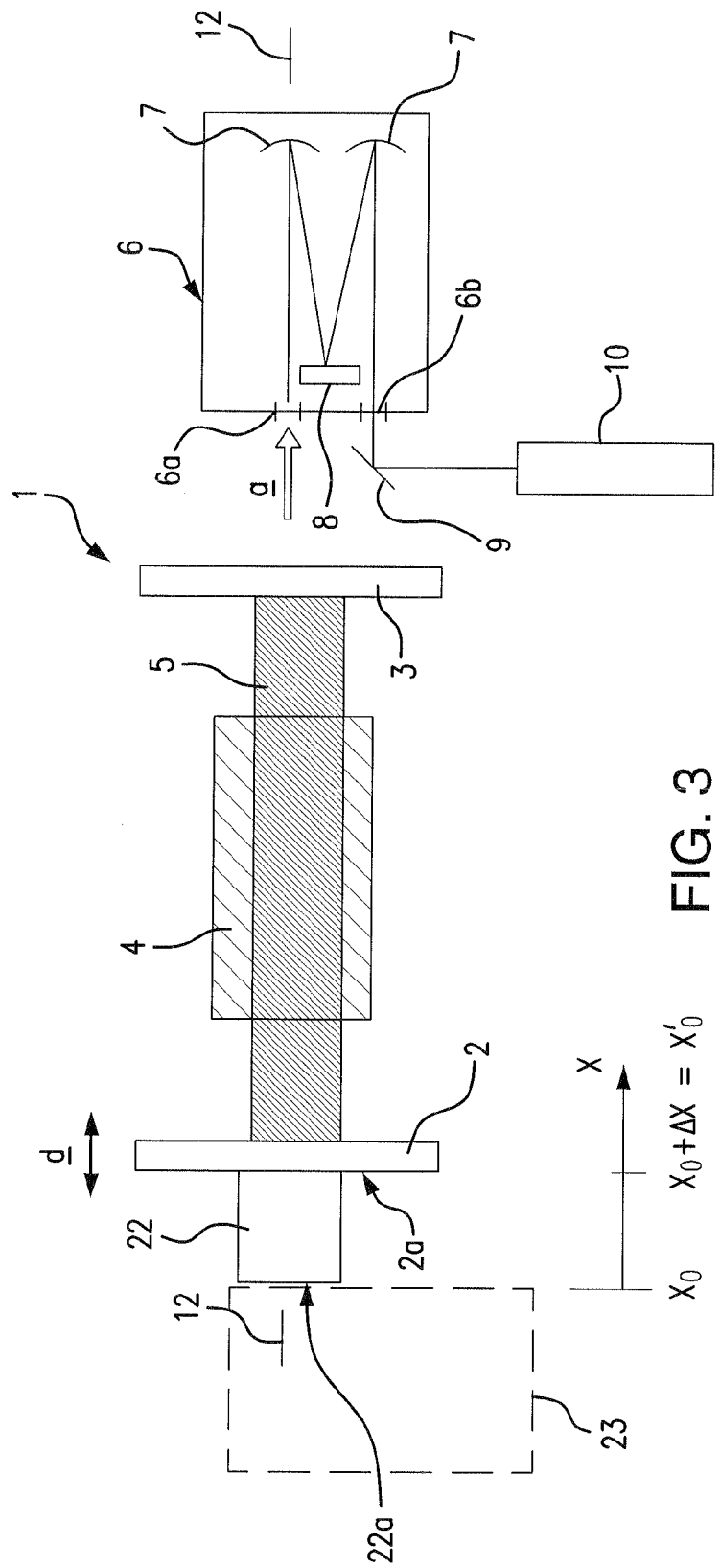
FIGS. 3 and 4 are representations corresponding to FIGS. 1 and 2 for a sensor device for measuring a length or change in length.

FIG. 3 shows an embodiment of a sensor device according to the invention, which is largely the same as the sensor device according to FIG. 1, for which reason the same reference numerals are used for like parts. In contrast to FIG. 1, the physical value affecting the emission behaviour of the laser 1 is here the length, so that the device according to FIG. 3 differs in two respects in particular from the device according to FIG. 1.

A first difference lies that the receiving space 14 for the fluid is absent. The active laser medium 4 is therefore without an interruption in FIG. 3, i.e. it is shown continuous.

A further essential difference from FIG. 1 lies in that the sensor device according to FIG. 3 serves to measure a length.

Figure 4A:
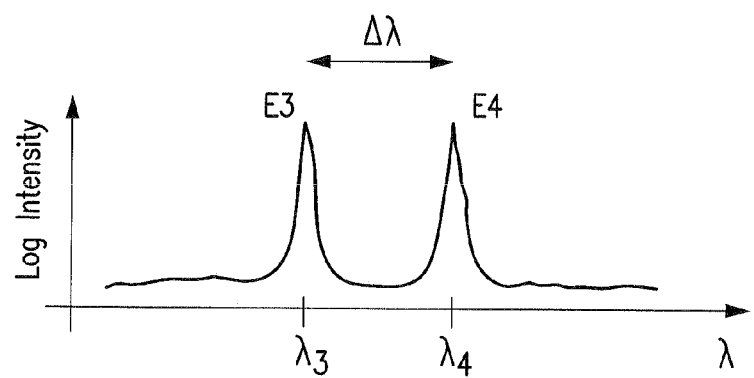

To this end the resonator mirror 3 for example is immovable, i.e. it is firmly fixed to a stationary component, while the resonator mirror 2 is mounted movably in the direction of a double arrow d by means which are not shown in detail. A measuring element 22, e.g. of rod form, is fixed on an outer side 2a of the resonator mirror 2 and has a face 22a remote from the resonator mirror 2, used as a reference for the length or change of length measurement and is positioned for this at an initial position $x_0$. In accordance with the invention the length measurement is effected by consideration of the changes which occur in the laser emission on account of a displacement of the measuring element 22 and thus also of the resonator mirror 2 in the direction of the double arrow d. As in the case of FIG. 1, the laser 1 is operated in dual mode. The emitted light (arrow a) is split up spectrally by means of the grating 8 and deflected on to the photodetector 10, in order to record its spectral intensity. The arrangement is such that an intensity/wavelength spectrum according to FIG. 4 results in the non-displaced state of the measuring element 2, having two main modes E3 and E4 like in FIG. 2, at wavelengths $\lambda_3$ and $\lambda_4$, which are emitted with substantially the same intensity.

Figure 4B:
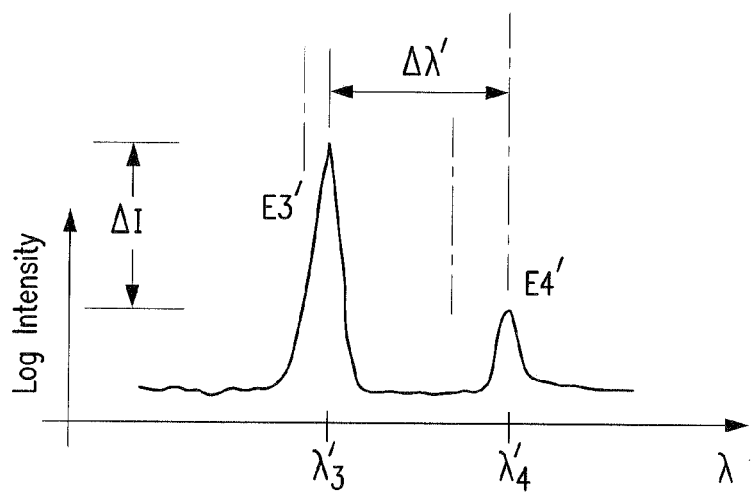

The measurement of a length presupposes for the purposed of the invention a corresponding displacement of the measuring element 22 or of the resonator mirror 2 through a path $\Delta x$ in the direction of the axis 12, as is shown much exaggerated in FIG. 3. In fact the amount $\Delta x$ amounts only to some nanometres or even femto- or atto-metres for example. On account of the immovably arranged resonator mirror 3 this results in a corresponding shortening of the geometric resonator length by the amount $\Delta x$. Since the laser 1 is operated in dual modes, where the two modes practically assume a bistable state, an extremely small change in the resonator geometry already leads to a marked change in the mode emission. A received intensity/wavelength spectrum of the laser emission following the reduction of the laser by the value $\Delta x$ is shown in FIG. 4(b). The modes E3 and E4 emitted initially with the same intensity are changed by the length change $\Delta x$ of the resonator into two modes E3' and E4', whose intensity maxima lie at wavelengths $\lambda_3'$ and $\lambda_4'$ and whose absolute spectral positions are each displaced, while the spectral spacing $\Delta\lambda'$ compared with the spacing $\Delta\lambda$ of the intensity maxima of the initial modes E3 and E4 may have altered. In particular, as FIG. 4(b) shows, a marked change in the intensity curve of the two modes E3, E4 and E3', E4' is observed, so that the measured value $\Delta I$ here also enables a sensitive indication of the length or change in length.

Whether the amount $\Delta I$ is better suited to for the length measuring than the amount $\Delta\lambda$ in a particular case has to be assessed for the individual case. Moreover, for measuring absolute lengths it would further be practicable to record a calibration curve, wherein the known values $\Delta I$ and $\Delta\lambda$ are associated with changes of resonator length measured with other means (e.g. a laser interferometer).

Alternatively, the sensor device according to FIG. 3 can also be used as a sensor for determining the temperature as a physical value. An object whose temperature is to be determine is placed in thermal contact for example with a good heat conductor body 23 arranged immovably, shown in broken lines in FIG. 3 and fixedly attached to the face side 22a of the measuring element 22. A thermal expansion or contraction of the measuring element 22 thus caused leads to a displacement of the resonator mirror 2, so long as it is ensured that the body 23 itself can only expand only in the direction of the resonator mirror 3. A displacement of the resonator mirror 2 under the influence of temperature changes leads in the same way as in the length measurement to a change of the mode properties, so that their measurement can be used as a measure of the temperature.

The pressure can serve as a further physical value. For example, a laser 25 shown schematically in FIG. 5 can be used for this, being formed as a double hetero-structure diode laser. Otherwise the device largely correspond to the device according to FIGS. 1 and 3, so that like parts are again given the same reference numerals and only the parts of the laser 25 necessary for an understanding of the invention are shown. The laser 25 is formed as a laminated body composed of different semiconductor layers 25a to 25e, wherein a middle layer 25c is laser active and two end faces of the laminated body are crystallographically split, optically enhanced with multiple layers or optically polished and are thus formed as resonator mirrors 25f, 25g. By suitable dimensioning of the laminated structure and the contact geometry of the laser 25, as well as through a suitable injection current for creating a population inversion, it is arranged that the laser 25 emits in accordance with the invention in at least two optical modes. These are coupled out of the laser 25 (arrow a) and analysed, as explained in detail above in conjunction with FIGS. 1 and 3.

If a pressure is exerted in the direction of the arrows p1 and p2 on the broad sides of the laser 25 or its thin, membrane like structure, the laser 25 deforms along lines of deformation shown very schematically and in broken lines. This change of the laser geometry affects the laser emission analogously to FIGS. 2 and 4, so that an inference regarding the pressure as a physical value can be made qualitatively or, after calibration, quantitatively, from a comparison of the changes of the at least two modes. Alternatively it would also be conceivable with suitable formation of the laser 25 to convert pressures acting in the direction of the axis 12 into a change in the spacing between the resonator mirrors 24f, 24g, in that these are formed for example as thin, flexible membranes under tension at the edge, and thus determine the pressure indirectly similarly to the temperature in FIG. 3 through a corresponding change of length.

Further embodiments of the sensor device according to the invention will now be described with reference to FIGS. 6 to 24. Since these embodiments differ from the embodiments according to FIGS. 1 to 5 essentially only in details of the laser or the structure of a laser component arranged between to resonator mirrors, but not in their dual or multimode operation, only different components of the laser will be explained in detail below. Moreover, the description is limited to the case of detecting a fluid on the basis of the spectral absorption as a physical value for the avoidance of repetitions.

FIGS. 6 to 9 show a laser component known per se with horizontal resonators (e.g. "A micro-machined in-plane tunable optical filter using a thermo-optic effect of crystalline silicon" by S. S. Yun and J. H. Lee in Micro-mechanics and micro-engineering, 13, 1-5 (2003)).

Figure 6:
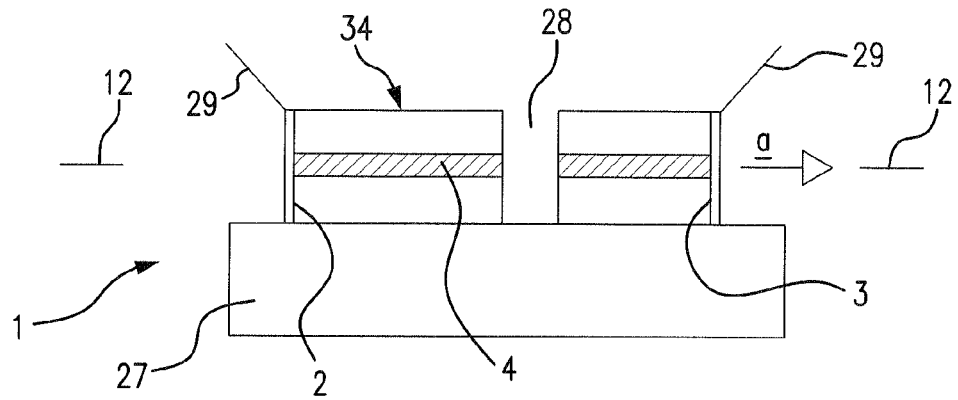
FIGS. 6 to 10 show further embodiments of a sensor device according to the invention for detecting and concentration measurement of a chemical substance.

According to FIG. 6, a heat sink 27 in the form of a Peltier element is additionally associated with the laser 1, mounted on the laser component with its resonator mirrors 2, 3, which here consist of vapour deposited coatings. The active laser medium 4 is interrupted along the horizontal axis 12 in accordance with the invention, like in FIG. 1, with formation of a fluid receiving space 28 which extends down to the heat sink 27. The laser 1 moreover comprises guide elements 29 arranged or formed like a funnel which divert the fluid in the direction of the receiving space 28 and are advantageous in particular with a fluid in the form of a liquid.

Figure 7:
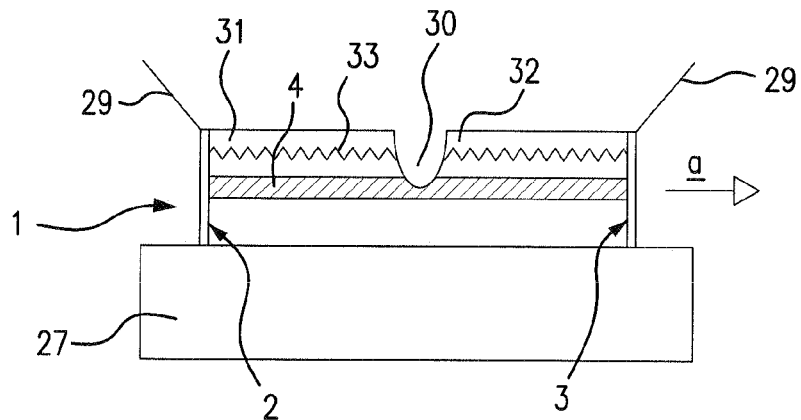

FIG. 7 shows an embodiment analogous to FIG. 6 of the sensor device according to the invention in which a receiving space 30 for the fluid formed like a groove passes only partially through the active laser medium 4. The receiving space 30 is bounded at the sides, above the laser active medium 4, i.e. on the side remote from the heat sink 28, by two layers 31, 32 in each of which a spatially periodic structure is provided in the form of a so-called DFB grating 33 providing spatially divided feedback (distributed feedback, DFB).

The lasers 1 shown in FIGS. 6 and 7 can in accordance with the invention also be a component of a sensor device provided for temperature measurement. Should the say temperature of an object under investigation (not shown) be for determination, the heat sink 27 is for example brought into good thermal contact with the object under investigation. Depending on the heat transferred from the object under investigation to the heat sink 27, a slight change in the spacing of the resonator mirrors 2, 3 is obtained, which analogously to the above description leads to a change in the emission spectrum of the laser 1.

Figure 8:
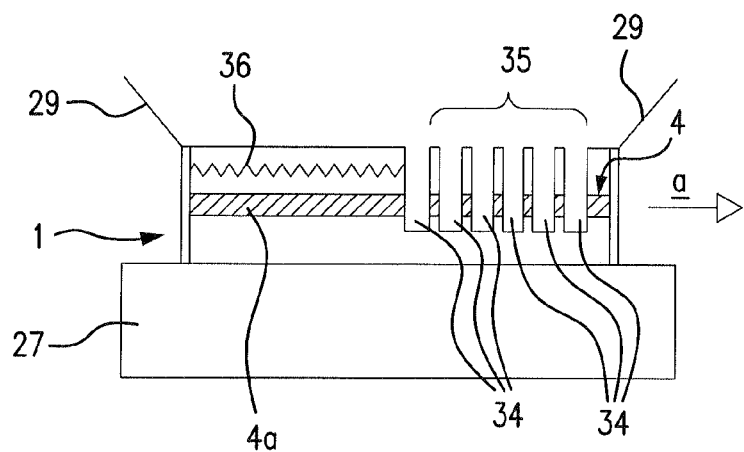
Figure 9:
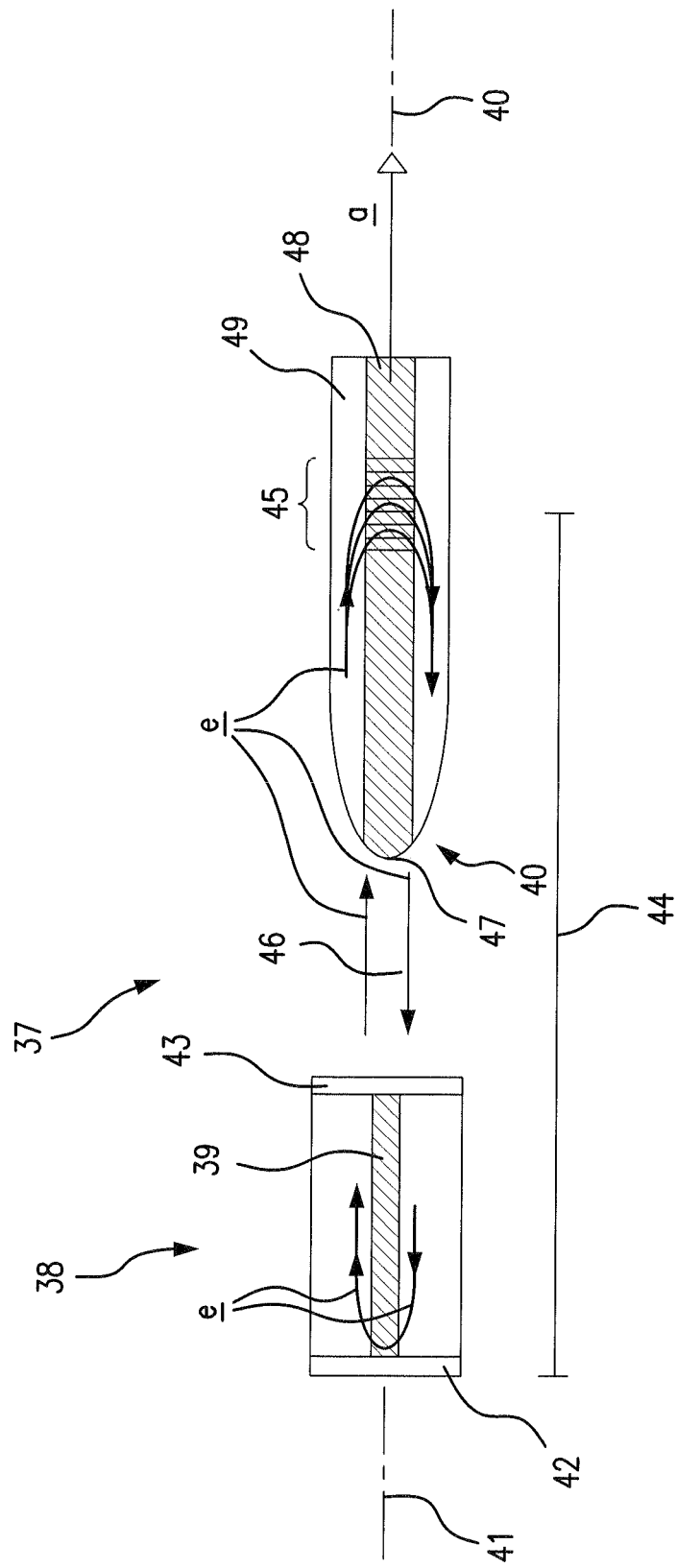

In the embodiment of the laser 1 shown in FIG. 8, a plurality of hollow spaces 34 is provided, which together form a receiving space for a fluid. The active medium 4 of the laser 1 is therefore interrupted several times. In the embodiment according to FIG. 8 a DFB grating 35 is moreover formed in the sections between the hollow spaces 34 and has a high refractive index contrast and thus a large coupling coefficient. A DFB grating 36 with a low coupling coefficient is provided in the non-interrupted section 4a of the laser medium 4.

As a comparison between FIGS. 6 to 8 shows, the respective receiving spaces 28, 30 and 34 can in principle be formed arbitrarily and arranged in the light path. Moreover the DFB grating 35 can be completely omitted (FIG. 6) or be disposed selectively on one side or both sides of the receiving space 30 (FIG. 7).

A laser used in a sensor device according to the invention can also be formed by a plurality of elements. One such laser 37 includes according to FIG. 9 a s-called Fabry-Perot laser component 38 formed in correspondence with FIG. 3, with an active laser material 39 and a coaxially arranged fibre 40, both arranged one after the other along an axis 41 along which the laser emission takes place. The laser component 38 is provided on one face with a highly reflecting coating (HR=high reflectivity) forming a resonator mirror 42, while the opposite face has a coating 43 with low reflectivity (AR=anti-reflection). A resonator 44 of the laser 37 is here formed on one side by the resonator mirror 42 and on the other side by a resonator mirror 45 in the form of a fibre grating provided in the fibre 40. The light circulations are shown simplified by arrows e. a receiving space 46 for the fluid is located between the laser component 38 and an end face 47 following along the axis 41 of the fibre 40 formed essentially by a fibre core 48. The fibre core 48 is surrounded from the face 47 up to the opposite end by a fibre sheath 49. The light a emitted from the laser is passed analogously to FIG. 2 to a measuring device, not shown.

Figure 10A:
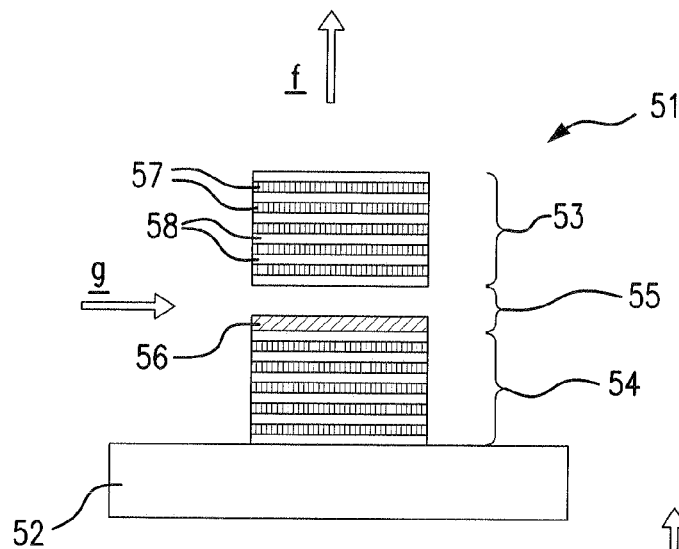
Figure 10B:
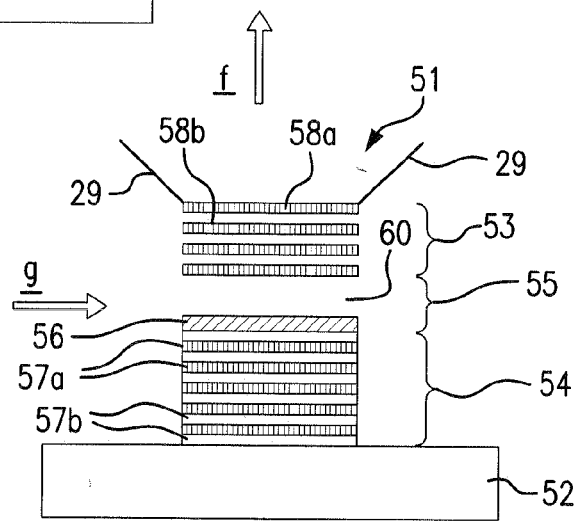
Figure 10C:
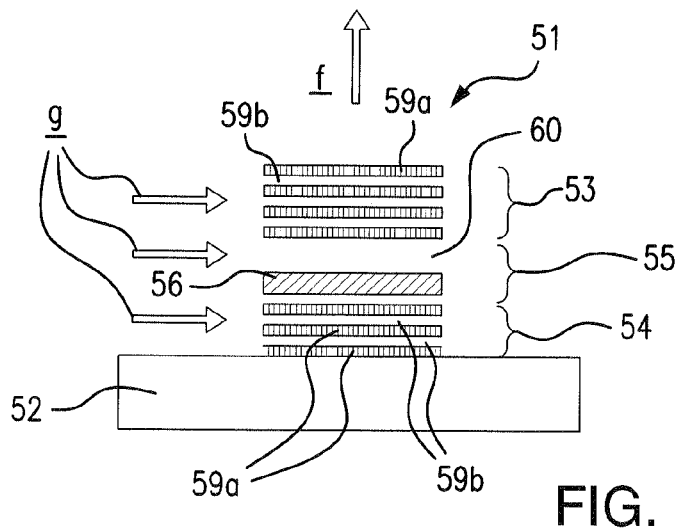

FIGS. 10(a) to 10(c) show the essential parts of a laser 51 with a vertical resonator (VCSEL=vertical cavity surface emitting laser). The basic structure of such a laser 51 which emits light upwards (vertically) in the direction of arrows f is known [e.g. "Ultra low biased widely continuously tunable Fabry-Perot Filter" by S. Irmer, J. Daleiden, V. Rangelov, C. Prott, F. Römer, M. Strassner, A. Tarraf, H. Hillmer in Pnot. Technol. Lett. 15, 434 (2003)]. The laser 51a includes a heat sink 52 on which is mounted a component which comprises two resonator mirrors 53 and 54 in the form of DBR mirrors (DBR=distributed Bragg reflector) and a cavity 55 disposed between these, in which an active laser medium 56 is disposed. The DBR or resonator mirrors 53, 54 are formed as laminated bodies with layer sequences of which three variants are shown by way of example in FIGS. 10(a) to 10(c).

According to FIG. 10(a) both resonator mirrors 53, 54 comprise alternating different solid body layers 57a and 57b. In the embodiment according to FIG. 10(b) the resonator mirror 54 comprises the alternating solid body layers 57a and 57b while the resonator mirror 53 comprises alternating solid body layers 58a and air layers 58b. Finally, according to FIG. 10(c), both resonator mirrors 53, 54 comprise alternating solid body layers 59a and air layers 59b. The air layers 58b and 59b open at the sides serve as receiving spaces, which are traversed in the direction of arrows g by the fluid to be investigated, which can also enter the remaining hollow space between the laser medium 56 and the resonator mirror 53. A gaseous fluid can flow on all sides round and through the component. In the case of a liquid the guide elements 39 described with reference to FIG. 6 are preferably employed [e.g. FIG. 10(b)], which direct the liquid stream like a funnel into the hollow spaces involved.

In accordance with the invention the laser 51 can be used to determine a fluid in that this is guided in the direction of the arrow g and transverse to the arrows f, either according to FIG. 10(a) solely through the hollow space 60, according to FIG. 10(b) through this and the air layers 58b of the resonator mirror 53 or according to FIG. 10(c) through the hollow space 60 and the air layers 58b, 59b of both resonator mirrors 53, 54. In this case these parts of the cavity 55 or the air layers 58b, 59a and 59b replace the receiving spaces 14, 28, 30, 34 and 46 provided in accordance with FIGS. 1 and 6 to 9. The embodiment according to FIG. 10(c) is at present regarded as the best for the purposes of the invention, because the fluid can enter numerous hollow spaces of the laser 51, whereby a high sensitivity results.

Figure 11:
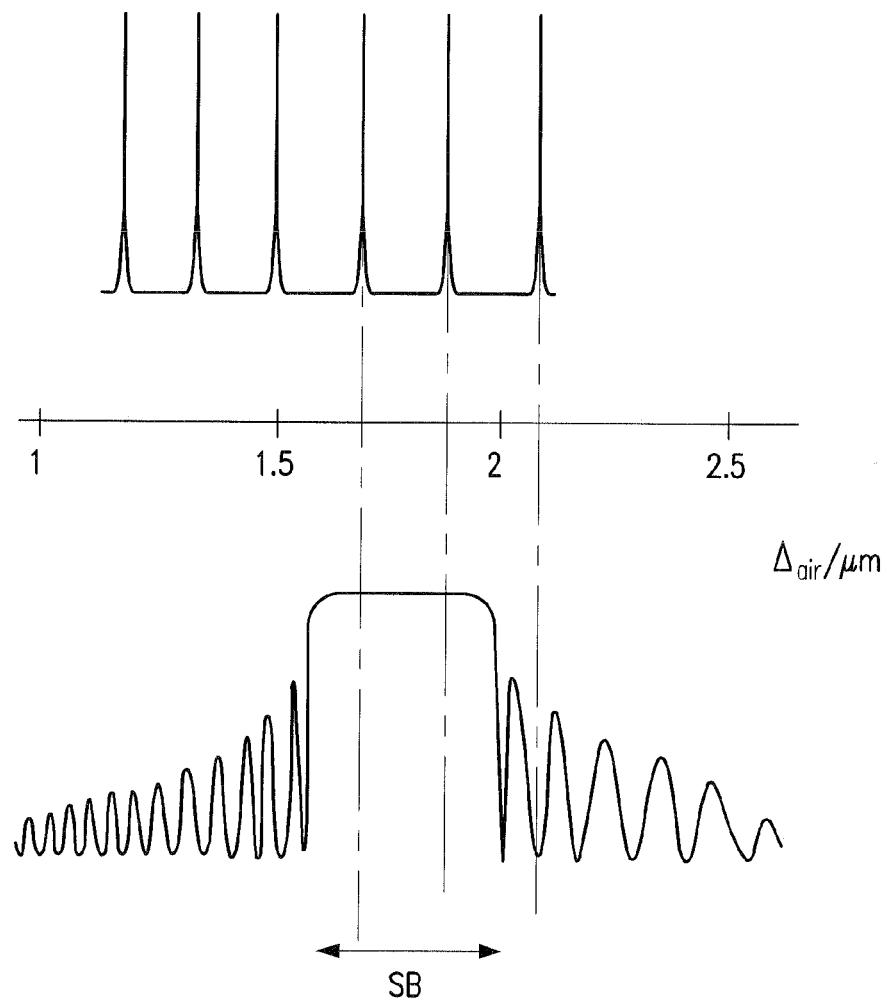
FIG. 11 is a schematic representation of the spectral dependence of the operating or measured values of the sensor device according to FIG. 10.

The identification according to the invention of a fluid using the laser 51 according to FIG. 10 takes place in accordance with FIG. 11 for example. FIG. 11 show an example above of a mode spectrum of the active laser medium 56 and below the reflection spectrum of the resonator mirrors 53 and 54. Because of the high refractive index contrast of the individual layers 57, 58 and 59 forming the resonator mirrors 53, 54, a stop band SB is very much extended spectrally. By selecting the length of the cavity 55 in the direction of the arrow f in FIG. 10 the laser modes are so established that just two modes come to lie in the region of highest reflectivity, i.e. in the stop band SB, as is indicated in FIG. 11 by the broken lines. Thus, as in the other embodiments a dual mode emitting laser is obtained. According to the invention, one of these two modes will brought spectrally to an absorption band or line of a fluid to be identified flowing through the laser 51, analogously to FIG. 2. Otherwise the procedure is as has been described with reference to FIG. 2.

Figure 12:
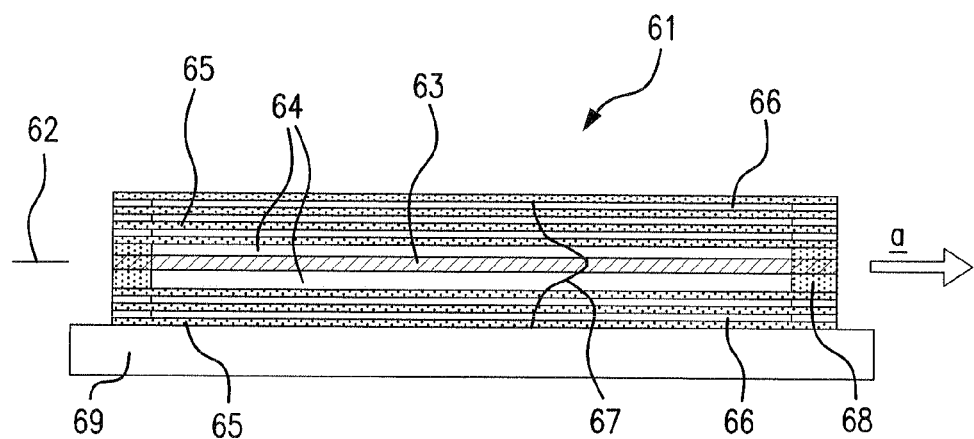

In the embodiment according to FIG. 12 a laser 61 comprises analogously to FIG. 1 a horizontal resonator not shown in detail, from which light is emitted along an axis 62 in the direction of the arrow a. An active laser medium 63 is disposed on the axis 62. On both sides thereof there are hollow spaces parallel to the axis 62 serving for a fluid, to which there adjoin two outer layer sequences, which are so formed alternately of membrane like solid body layers 65 and air layers 66, which are so formed that a schematically shown intensity curve 67 for the modes results in the direction of the axis 62. The solid body layers 65 are spaced by retaining bodies 68, which on the one hand enable the gas to be investigated to pass through the receiving space 64, on the other hand to support the whole component on a substrate or heat sink 69.

Figure 13:
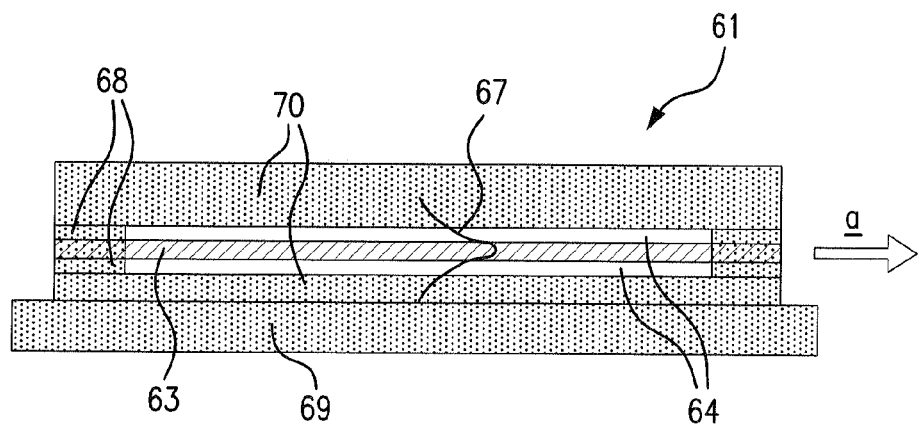

The embodiment according to FIG. 13 differs from the embodiment according to FIG. 12 only in that the multi membrane structure containing a plurality of layers 65, 66 is replaced by two outer material layers 70, which have a smaller refractive index than the active laser medium 63. The fixing of the partially free-floating membranes on the heat sink 69 is effected with retaining blocks not shown in detail.

The light is, as the intensity curve 67 shows, guided horizontally in both embodiments, wherein the light modes each extend over the receiving space 64 through which fluid flows.

Figure 14:
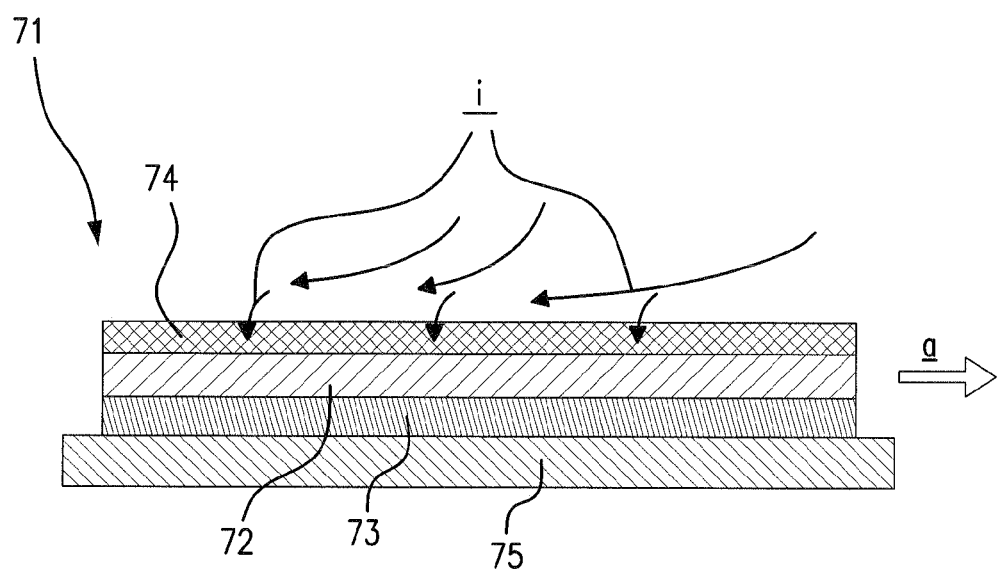

In a variant shown in FIG. 14, the modes of a laser 71 are guided in a horizontal waveguide resonator. Two different layers 73 and 74 adjoin the two sides of an active laser medium 72, both having a smaller refractive index than the active laser medium 72. The one, inner layer 73 is mounted on a substrate 75 (or a heat sink) while the other, outer layer 74 is so implemented that it can receive components of the fluid to be identified, as is indicated by the arrow i. The concentration of the fluid in the outer layer 74, which here forms the receiving space for the fluid is however so small that the refractive index does not change. The fluid components can be diffused particles or molecule agglomerates of a gas for example. The fluid or the components penetrating the layer 74 affect the laser modes guided in the waveguide resonator analogously to the above description. On the basis of the resulting changes of the emission behaviour of the laser 71 the fluid can be identified.

Figure 15:
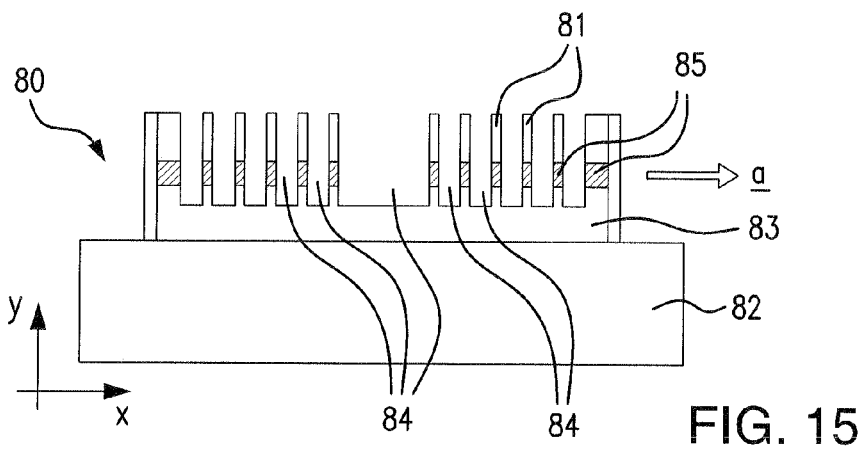
Figure 16:
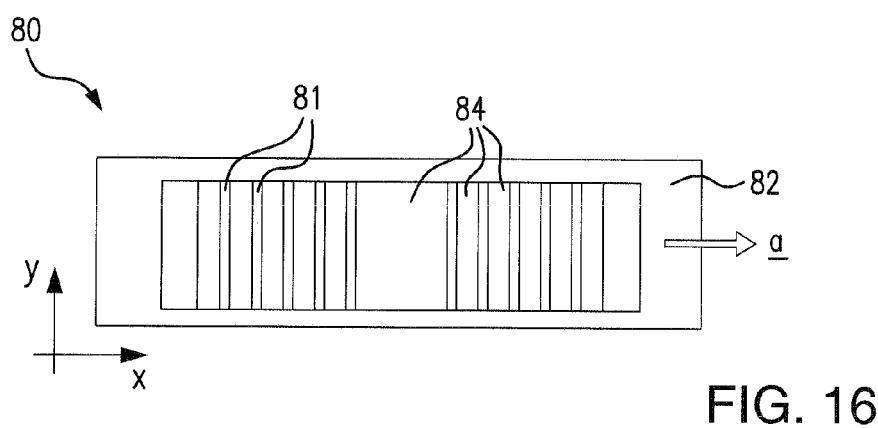

According to a further embodiment shown in FIGS. 15 and 16 in longitudinal section and a plan view, the resonator of a laser 80 is formed as a DBR reflector with a customary rib structure, which includes a plurality of ribs 81 which stand out perpendicularly from a component 83 arranged on a heat sink 82 and are spaced in the direction a of laser emission by hollow spaces 84. Each rib 81 contains part of a laser active medium 85. The hollow spaces 84 are open on at least one side and/or at the top and accordingly at the same time form a receiving space for a fluid.

Figure 17:
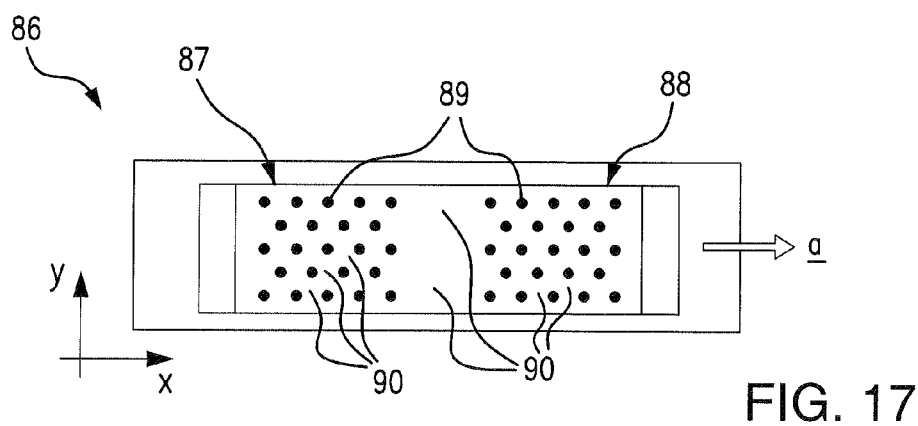

In a further embodiment of the invention shown in FIG. 17, a laser 86 includes two resonator mirrors 87, 88 in the form of photonic crystals, which each comprise a plurality of regularly arranged columns 89. Each column 89 contains a part of a laser active medium, not shown individually. The columns 89 are so arranged in parallel rows that the laser light is emitted in the direction of the arrow a (x-direction), as in the embodiment according to FIG. 1. A fluid to be identified is passed into a receiving space, which is formed by the hollow spaces 90 formed between the columns 89. FIG. 27 shows a plan view corresponding to FIG. 16, so that a longitudinal section through the columns 89 corresponds with FIG. 15.

Figure 18:
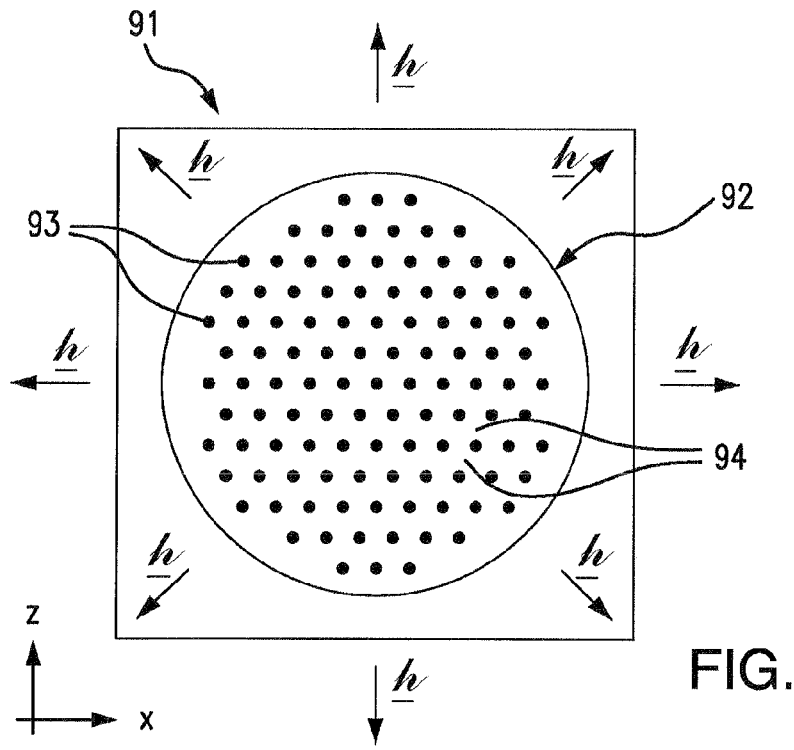
Figure 22:
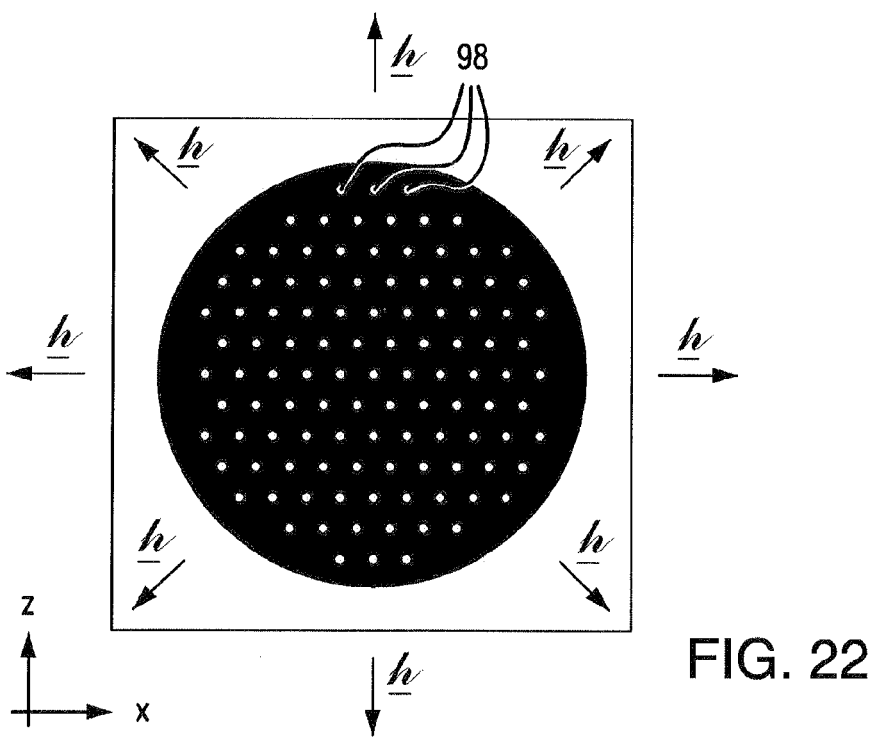

The embodiment of a laser 91 according to FIG. 18 differs from that according to FIG. 17 in that the resonator of the laser 91 is formed by a photonic crystal 92 with a plurality of columns 93 which are arranged in rows which run out essentially radially from a common centre. The radiation of laser light therefore takes place here radially in the direction of a plurality of arrows h, which lie in a zx-plane as usually conceived. Hollow spaces 94 remaining free between the columns 93 form a receiving space for a fluid. Emission perpendicular to the plane of the figure is also possible with a suitably modified arrangement of the grating.

Figure 19:
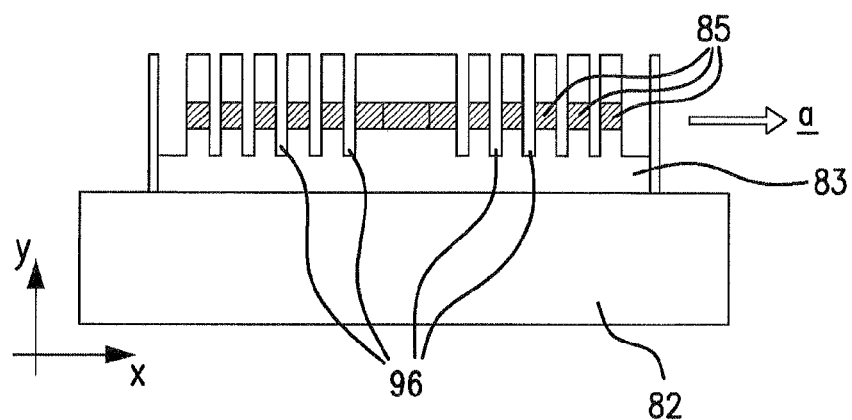
Figure 20:
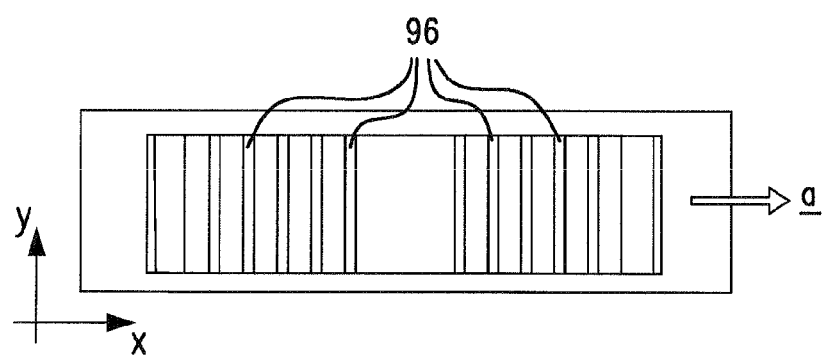
Figure 21:
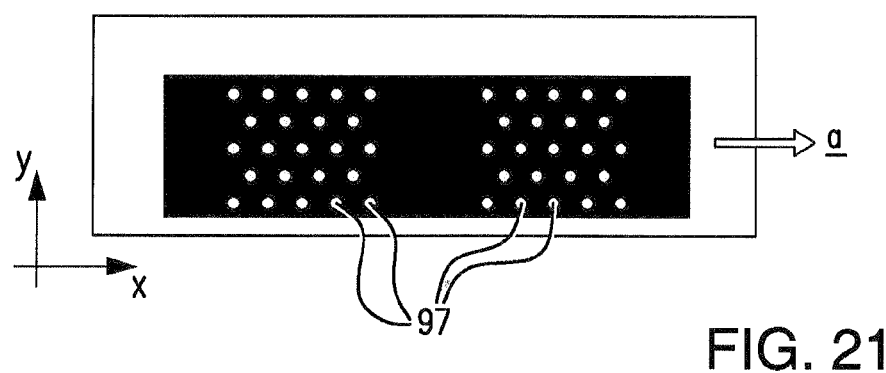

While in the embodiments according to FIGS. 15 to 18 the receiving space for the fluid formed from the hollow spaces 84, 90 and 94 respectively is comparatively large and the space occupied by the active laser medium (e.g. 85) is comparatively small, the arrangement in the corresponding embodiments shown in FIGS. 19 to 22 has an inverse construction in each case. Instead of the ribs or columns 81 or 89, 93 respective tubular holes 96, 97 and 98 are formed in the component 83 or photonic crystals as fluid receiving spaces. As FIGS. 19 and 20 show, the space for the laser medium 85 which can be accommodated in the remaining zones of the component 83 is increased while at the same time the space for the fluid provided by the holes 96 is correspondingly reduced. Otherwise the embodiments according to FIGS. 19 to 22 correspond to those according to FIGS. 21 and 22.

Finally, FIGS. 23 and 24 show a laser 102 and 103 respectively with photonic crystals 104 and 105, in which defect rows 106 and 107 respectively are provided, which with suitable dimensioning have waveguide characteristics. According to FIG. 23 the defect rows 106 are formed by defect sections which contain the laser active layer. In between the defect sections 108 or defect rows 106 there is a receiving space 109 for a fluid. In the case of FIG. 24 the defect rows 107 are formed from tubular holes 110 in the photonic crystal 105, which form a receiving space for a fluid. The active laser medium is here located in the material layers of the photonic crystal 105 surrounding the defect rows 107 or holes 110. The laser light is radiated parallel to the defect rows 106, 107 (arrow a), since the arrangement is such that horizontal resonators are present.

The invention is not limited to the embodiments described here and shown in the accompanying drawings, which can be modified in many different ways. Thus the invention also provides for the measurement of a change of volume through conversion into a corresponding change of length Likewise the invention comprises measurement of heat energy or its change as well as measurement of a heat energy flow or its change. The values are detected, as described, in each case through the effects which they or their changes have on the at least two emitted modes or the emission behaviour of the laser. In like manner, optical refractive indices of components inserted in the lasers of the sensor devices according to the invention, or their temperature dependence on temperature, the electrical and magnetic field or a radiation intensity or the like can be detected and be determined by determining the difference between the intensity maxima of the modes emitted by the lasers. In this manner highly sensitive sensors for magnetic fields, electric fields, changes in heat energy and electromagnetic radiation can be constructed. It would also be possible so to form the sensor devices that length, pressure and absorption can be detected individually or in combination as physical values through a fluid in a single device.

Furthermore, instead of the grating structure of first order shown with the horizontal resonators, which effect a horizontal laser emission (arrow a), gratings of higher order (e.g. second order) can be used. The light will thus be radiated in the vertical, i.e. y-direction (e.g. arrow f in FIG. 10). This is very advantageous in particular when the identification of fluid is effected through an optical measurement.

As lasers for the purposes of the present invention there can be considered semiconductor lasers such as hetero-structure diode lasers of III-V semiconductors, quantum well lasers, II-VI diode lasers, solid body lasers such as Nd:YAG lasers for example or fibre lasers. Lasers which facilitate a miniaturised structure of the sensor device according to the invention are especially preferred.

Figure 5:
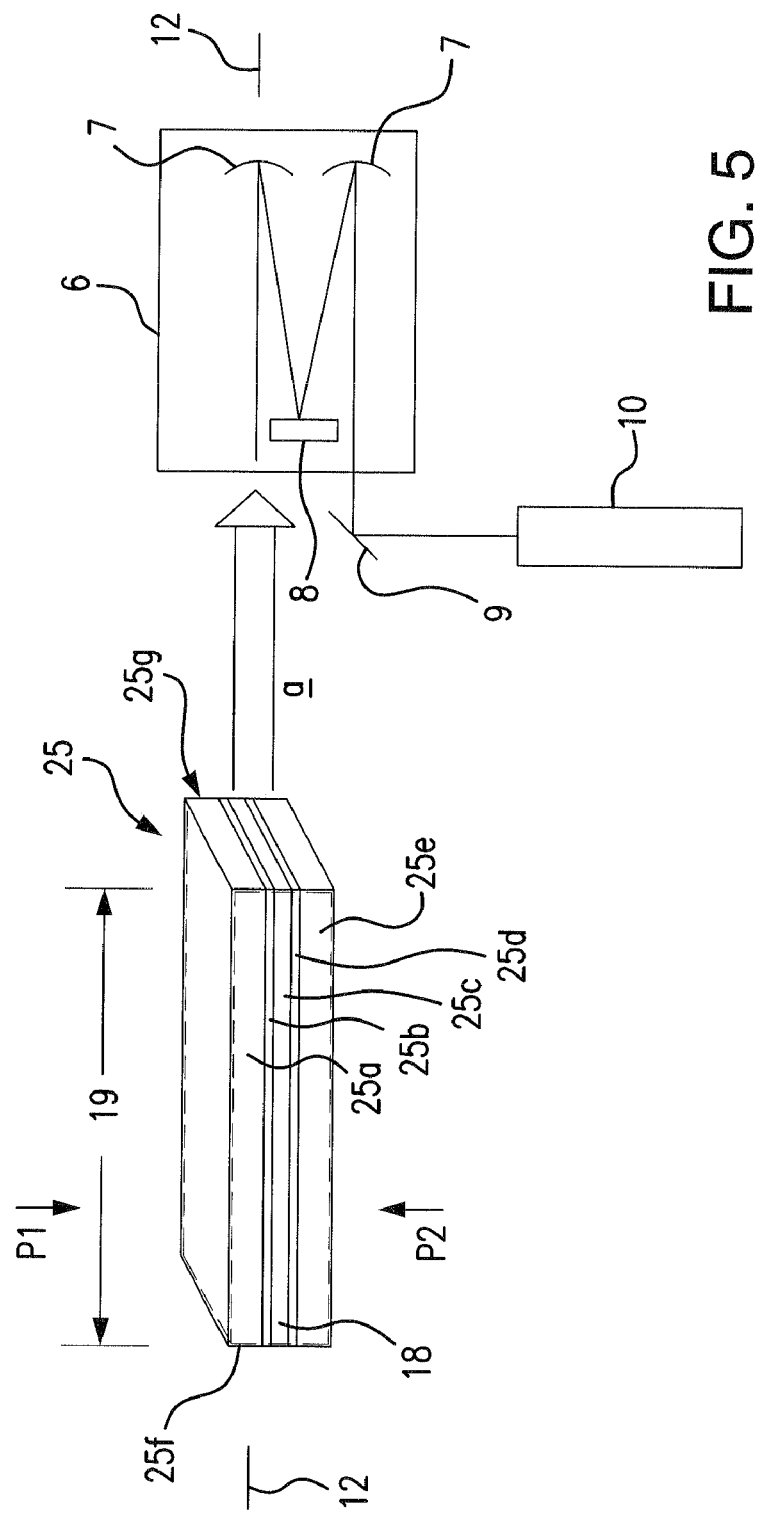
FIG. 5 shows parts of a sensor device according to the invention schematically, for measuring a pressure or change of pressure.

In relation to the measurement of the light emitted by the sensor device according to the invention, it is possible in all described variants to do away with the monochromatic filter 6 shown in FIGS. 1, 3 and 5 and to use a diode array instead of the photodetector 10, which can receive the light intensity at a plurality of wavelengths simultaneously. Likewise it is also conceivable the perform the intensity measurement by using a filter and a photodetector not selective as to wavelength but integrally for a certain range determined by the transmission characteristic of the filter. Finally, it will be understood that the various features can also be used in combinations other than those shown in the drawings.

The invention claimed is:

1. A sensor device for determining a physical value of a substance, comprising
   a laser whose emission behavior is affected by the physical value and which emits at least two competing modes (E1, E2, E1', E2', E3, E4) lying above a laser threshold;
   a measuring device for receiving a relative intensity noise (RIN) of the laser for a determination of intensities or intensity difference of the modes emitted by the laser; and
   means providing a comparison between intensities of at least two of the modes (E1, E2, E1', E2', E3, E4) occurring under an influence of the physical value and, based on the comparison, producing a signal indicative of the physical value of the substance.

2. A sensor device according to claim 1, wherein the comparison means form a difference ($\Delta I$) between spectral intensity maxima of the at least two modes (E1, E2, E1', E2', E3, E4).

3. A sensor device according to claim 1, further comprising an optical detection system for measuring a spectral intensity distribution of a radiation emitted from the laser.

4. A sensor device according to claim 1, wherein the laser is a solid body laser.

5. A sensor device according to claim 1, wherein it is arranged to determine an optical absorption through a chemical substance having at least one optical absorption band (A) as the physical value.

6. A sensor device according to claim 5, further comprises a receiving space for a fluid within a resonator of the laser.

7. A sensor device according to claim 6, wherein the receiving space is formed as at least one interruption in an active laser material.

8. A sensor device according to claim 6, wherein the receiving space includes hollow spaces remaining free between columns of photonic crystals.

9. A sensor device according to claim 6, wherein the receiving space is formed by tubular holes of photonic crystals.

10. A sensor device according to claim 6, wherein the receiving space includes at least one hollow space which is disposed between two resonator mirrors formed by DBR mirrors.

11. A sensor device according to claim 5, wherein the laser is formed to emit a corresponding number of the modes (E1, E2, E1', E2', E3, E4), of which each mode is tuned to an absorption band (A) of one of the substances, to determine the absorption by a plurality of chemical substances.

12. A sensor device according to claim 5, wherein the laser is arranged to emit a number (k) of the modes (E1, E2, E1', E2', E3, E4) which is at least one greater than a plurality (k−1) of the substances, with all other modes (k−1) apart from a mode serving as a reference mode tuned simultaneously to an absorption band (A) of one each of the substances to determine the absorption of the plurality (k−1) of the chemical substances.

13. A sensor device according to claim 1, wherein the laser has a horizontal resonator.

14. A sensor device according to claim 13, wherein the horizontal resonator includes resonator mirrors formed as photonic crystals.

15. A sensor device according to claim 1, wherein the laser has a vertical resonator.

16. A sensor device according to claim 15, wherein at least one of the resonator mirrors includes a layer sequence of at least one solid body layer and at least one air layer forming the receiving space for a fluid.

17. A method of determining a physical value using a laser by affecting its emission behavior by means of the physical value, comprising the steps of
   operating the laser to emit at least two competing modes (E1, E2, E1', E2', E3, E4) lying above a laser threshold,
   determining the intensities of the at least two modes (E1, E2, E1', E2', E3, E4) by measuring a relative intensity noise (RIN) of the laser,
   determining the physical value by comparing those intensities which result in relation to at least two of the modes (E1, E2, E1', E2', E3, E4) under an influence of the physical value by a detector, and
   based on the comparison, and producing a signal indicative of the physical value of the substance.

18. A method according to claim 17, further comprising determining the at least two modes (E1, E2, E1', E2', E3, E4) by optical spectroscopy.

19. A method according to claim 17, further comprising effecting the comparison by formation of a difference ($\Delta I$) between spectral intensity maxima of the at least two modes (E1, E2, E1', E2', E3, E4).

20. A method according to claim 17, further comprising employing at least one of a longitudinal mode, a transverse electrical mode and a magnetic mode as the modes (E1, E2, E1', E2', E3, E4).

21. A method according to claim 17, further comprising operating the laser with the at least two modes (E1, E2, E1', E2', E3, E4) which have different polarisations.

22. A method according to claim 17, further comprising effecting calibration measurements for quantitative determination of the physical value.

23. A method according to claim 17, further comprising determining an optical absorption (A) by a chemical substance as the physical value.

24. A method according to claim 23, further comprising operating the laser so that it radiates a plurality (k) of the modes (E1, E2, E1', E2', E3, E4) and is turning the laser so that the plurality (k) of the modes (E1, E2, E1', E2', E3, E4) apart from one mode each matches spectrally an absorption band (A) of a smaller plurality (k−1) of chemical substances and in that at least one mode which is associated with none of the substances is used as a reference mode.

25. A method according to claim 23, further comprising operating the laser so that a plurality (k) of the modes (E1, E2, E1', E2', E3, E4) is radiated and so tuned for determining the absorption which is affected by different substances that each one of the modes spectrally matches an absorption band (A) of one of the substances.

26. A method according to claim 17, further comprising determining a length, a pressure, a magnetic or electric field, an electromagnetic radiation energy, a temperature, a heat energy, a radiation power or a value derived therefrom as the physical value.

27. A sensor device for determining a physical value of a substance, comprising a laser whose emission behavior is affected by the physical value the laser and which emits at least two competing modes (E1, E2, E1', E2', E3, E4) lying above a laser threshold; means providing a comparison between intensities of at least two of the modes (E1, E2, E1', E2', E3, E4) occurring under an influence of the physical value, to effect a determination of the physical value; and means for using the physical value so determined to identify a substance, wherein the sensor device is arranged to determine an optical absorption through a chemical substance having at least one optical absorption band (A) as the physical value, wherein the laser is arranged to emit a number (k) of the modes (E1, E2, E1', E2', E3, E4) which is at least one greater than a plurality (k−1) of the substances, with all other modes (k−1) apart from a mode serving as a reference mode tuned simultaneously to an absorption band (A) of one each of the substances to determine the absorption of a plurality (k−1) of chemical substances.

28. A method of determining a physical value using a laser by affecting its emission behavior by means of the physical value, comprising the steps of operating the laser to emit at least two competing modes (E1, E2, E1', E2', E3, E4) lying above a laser threshold, determining the physical value by comparing those intensities which result in relation to at least two of the modes (E1, E2, E1', E2', E3, E4) under an influence of the physical value, identifying a substance based on the determined physical value, determining an optical absorption (A) by a chemical substance as the physical value, and operating the laser so that a plurality (k) of the modes (E1, E2, E1', E2', E3, E4) is radiated and so tuned for determining the absorption which is affected by different substances that each one of the modes spectrally matches an absorption band (A) of one of the substances.

* * * * *